US011644472B2

(12) United States Patent
Andres et al.

(10) Patent No.: US 11,644,472 B2
(45) Date of Patent: May 9, 2023

(54) CIRCULATING ANGIOPOIETIN-2 (ANG-2) FOR THE PREDICTION OF RECURRENCE OF ATRIAL FIBRILLATION

(71) Applicant: Roche Diagnostics Operations, Inc., Indianapolis, IN (US)

(72) Inventors: Herbert Andres, Penzberg (DE); Dirk Block, Bichl (DE); Johann Karl, Peissenberg (DE); Peter Kastner, Murnau am Staffelsee (DE); Ursula-Henrike Wienhues-Thelen, Krailling (DE); Roberto Latini, Milan (IT); Serge Masson, Monza (IT); Andre Ziegler, Laeufelfingen (CH); Edelgard Kaiser, Huenenberg See (CH); Stefan Palme, Bichl (DE); Markus Thomas, Rheinfelden (DE); Simona Barlera, Tradate (IT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 16/217,612

(22) Filed: Dec. 12, 2018

(65) Prior Publication Data

US 2019/0353666 A1 Nov. 21, 2019

Related U.S. Application Data

(63) Continuation of application No. PCT/EP2017/064970, filed on Jun. 19, 2017.

(30) Foreign Application Priority Data

Jun. 17, 2016 (EP) ..................................... 16174910

(51) Int. Cl.
*G01N 33/53* (2006.01)
*G01N 33/68* (2006.01)

(52) U.S. Cl.
CPC ..... *G01N 33/6887* (2013.01); *G01N 33/6893* (2013.01); *G01N 2800/326* (2013.01)

(58) Field of Classification Search
None
See application file for complete search history.

(56) References Cited

U.S. PATENT DOCUMENTS

| | | | |
|---|---|---|---|
| 4,016,043 A | 4/1977 | Schuurs et al. | |
| 4,018,653 A | 4/1977 | Mennen | |
| 4,424,279 A | 1/1984 | Bohn et al. | |
| 5,545,566 A * | 8/1996 | Growden | G01N 33/92 436/71 |
| 2008/0267971 A1* | 10/2008 | Green | A61P 13/12 536/23.53 |
| 2009/0062671 A1* | 3/2009 | Brockway | A61B 5/0031 600/518 |
| 2010/0124756 A1* | 5/2010 | Ray | G01N 33/6896 435/7.94 |
| 2010/0137420 A1* | 6/2010 | Nath | C07K 14/8139 514/453 |
| 2010/0159608 A1* | 6/2010 | Hess | G01N 33/6863 436/86 |
| 2010/0285491 A1 | 11/2010 | Wienhues-Thelen et al. | |
| 2011/0008804 A1* | 1/2011 | Kain | G01N 33/569 435/7.92 |
| 2011/0009861 A1 | 1/2011 | Mukherjee et al. | |
| 2012/0142012 A1* | 6/2012 | Hacker | G01N 33/57419 435/6.12 |
| 2013/0323719 A1 | 12/2013 | Cysewski et al. | |
| 2013/0338194 A1 | 12/2013 | Mukcherjee et al. | |
| 2015/0233946 A1 | 8/2015 | Block et al. | |
| 2017/0121774 A1* | 5/2017 | Vallania | C12Q 1/6883 |

FOREIGN PATENT DOCUMENTS

| | | |
|---|---|---|
| WO | 2008/089994 A1 | 7/2008 |
| WO | 2012/065095 A2 | 5/2012 |
| WO | 2012/107419 A1 | 8/2012 |
| WO | 2014/072500 A1 | 5/2014 |
| WO | 2014152828 A1 | 9/2014 |
| WO | 2015/140571 A1 | 9/2015 |
| WO | 2016/012783 A1 | 1/2016 |

OTHER PUBLICATIONS

Ammerer-Lercher et al., Analysis of Circulating Forms of proBNP and NT-proBNP in Patients with Severe Heart Failure, Clin. Chem. (2008), 54(5), p. 858-865. (Year: 2008).*
Qi et al., Effects of different peptide fragments derived from proadrenomedullin on gene expression of adrenomedullin gene, Peptides, (2002), 23, p. 1141-1147. (Year: 2002).*
Van Der Vekiens et al., Human and equine cardiovascular endocrinology: beware to compare, Cardiovascular Endocrinology 2013, vol. 2, No. 4, pp. 67-76 (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Helfrich et al., Angiopoietin-2 levels are Associated with Disease Progression in Metastatic Malignant Melanoma, Clin Cancer Res 2009; 15(4), pp. 1384-1392. (Year: 2009).*
Hijazi, Ziad, Digital Comprehensive Summaries of Uppsala Dissertations, New Risk Markers in Atrial Fibrillation, Acta Universitatis Upsaliensis Uppsala, 2013, pp. 1-76. (Year: 2013).*

(Continued)

*Primary Examiner* — Gary Counts
(74) *Attorney, Agent, or Firm* — Stinson LLP

(57) ABSTRACT

A method for predicting the risk of recurrence of Atrial Fibrillation in a subject based on measuring the amount of the biomarker Angiopoietin-2 (Ang-2) and optionally of at least one further biomarker in a sample from the subject is described. Also described is a method of diagnosing Atrial Fibrillation in a subject suspected to suffer from Atrial Fibrillation based on measuring the amount of the biomarker Angiopoietin-2 (Ang-2) and optionally of at least one further biomarker in a sample from the subject. Also described are devices adapted to carry out the method of the present disclosure.

9 Claims, 3 Drawing Sheets

(56) References Cited

OTHER PUBLICATIONS

Kin et al., Development of a novel automated ELISA analyzer based on an electrochemical detector, Proceedings of the 32 ISR (International Symposium on Robotics), Apr. 19-21, 2001, pp. 439-443. (Year: 2001).*

Anderson, Page A. W. et al., Molecular Basis of Human Cardiac Troponin T Isoforms Expressed in the Developing, Adult, and Failing Heart, Circulation Research, 1995, pp. 681-686, vol. 76.

Cheung, Anthony H. et al., Endothelial Tie2/Tek Ligands Angiopoietin-1 (ANGPT1) and Angiopoietin-2 (ANGPT2): Regional Localization of the Human Genes to 8q22.3-q23 and 8p23, Genomics, 1998, pp. 389-391, vol. 48, Issue 3.

Choudhury, Anirban et al., Relationship of Soluble CD40 Ligand to Vascular Endothelial Growth Factor, Angiopoietins, and Tissue Factor in Atrial Fibrillation A Link Among Platelet Activation, Angiogenesis, and Thrombosis?, Chest, 2007, pp. 1913-1919, vol. 132, No. 6.

Chugh, Sumeet S. et al., Worldwide Epidemiology of Atrial Fibrillation A Global Burden of Disease 2010 Study, Circulation, 2014, pp. 837-847, vol. 129.

Disertori, Marcello et al., Rationale and design of the GISSI-Atrial Fibrillation trial: a randomized, prospective, multicentre study on the use of valsartan, an angiotension II AT1-receptor blocker, in the prevention of atrial fibrillation recurrence, Journal of Cardiovascular Medicine, 2006, pp. 29-38, Abstract only, vol. 7, Issue 1.

Eckstein, Jens et al., Transmural Conduction is the Predominant Mechanism of Breakthrough During Atrial Fibrillation, Circulation, Arrhythmia and Electrophysiology, 2013, pp. 334-341, vol. 6.

Ferrieres, Gaelle et al., Human cardiac troponin I: precise identification of antigenic epitopes and prediction of secondary structure, Clinical Chemistry, 1998, pp. 487-493, vol. 44, No. 3.

Freestone, B. et al., Angiopoietin-2 is related in atrial figrillation: Implications for the prothrombotic state, European Heart Journal, 2004, pp. 488-489, Abstract No. P2923, vol. 25, No. Supp. S.

Freestone, Bethan et al., Angoegenic factors in atrial fibrillation: A possible role in thrombogenesis?, Annals of Medicine, 2005, pp. 370-371, vol. 37, No. 5.

Fuster, Valentin et al., 2011 ACCF/AHA/HRS Focused Updates Incorporated Into the ACC/AHA/ESC 2006 Guidelines for the Management of Patients With Atrial Fibrillation A Report of the American College of Cardiology Foundation/American Heart Association Task Force on Practice Guidelines, Circulation, 2011, pp. e269-e367, vol. 123.

Fuster, Valentin et al., ACC/AHA/ESC 2006 Guidelines for the Management of Patients With Atrial Fibrillation, Circulation, 2006, pp. e257-e354, vol. 114, No. 7.

International Search Report dated Aug. 3, 2017, in Application No. PCT/EP2017/064970, 5 pps.

Kerr, Charles R. et al., Progression to chronic atrial fibrillation after the initial diagnosis of paroxysmal atrial fibrillation: Results from the Canadian Registry of Atrial Fibrillation, American Heart Journal, 2005, pp. 489-496, vol. 149.

Kümpers, Philipp et al., Excess circulating angiopoietin-2 is a strong predictor of mortality in critically ill medical patients, Critical Care, 2008, 9 pp., vol. 12, R147.

Latini, R. et al., Circulating cardiovascular biomarkers in recurrent atrial fibrillation: data from the GISSI-Atrial Fibrillation Trial, Journal of Internal Medicine, 2011, pp. 160-171, vol. 269.

Lukasz, Alexander et al., Angiopoietin-2 in Adults with Congenital Heart Disease and Heart Failure, PLoS, 2013, e66861, 8 pp., vol. 8, No. 6.

Maisonpierre, Peter C. et al., Angiopoietin-2, a Natural Antagonist for Tie2 That Disrupts in vivo Angiogenesis, Science, 1997, pp. 55-60, vol. 277.

Masson, Serge et al., Predicting atrial fibrillation recurrence with circulating inflammatory markers in patients in sinus rhythm at high risk for atrial fibrillation: data from the GISSI atrial fibrillation trial, Heart, 2010, pp. 1909-1914, vol. 96.

Ono, Yasuhiro et al., Expression of prostacyclin-stimulating factor, a novel protein, in tissues of Wistar rats and in cultured cells, Biochemical and Biophysical Research Communications, 1994, pp. 1490-1496, vol. 202, No. 3.

Pöss, Janine et al., Angiopoietin-2 and outcome in patients with acute decompensated heart failure, Clinical Research in Cardiology, 2015, pp. 380-387, vol. 104.

Richter, Mark M., Electrochemiluminescence (ECL), Chemical Reviews, 2004, pp. 3003-3036, vol. 104.

Staszewsky, Lidia et al., Cardiac Remodeling, Circulating Biomarkers and Clinical Events in Patients with a History of Artrial Fibrillation. Data from the GISSI-AF Trial, Cardiovascular Drugs and Therapy, 2015, pp. 551-561, vol. 29.

Van Marion, Denise M. S. et al., Diagnosis and Therapy of Atrial Fibrillation: the Past, the Present and the Future, Journal of Atrial Fibrillation, 2015, pp. 51-60, vol. 8, Issue 2.

Wong, Adrianne L. et al., Tie2 Expression and Phosphorylation in Angiogenic and Quiescent Adult Tissues, Circulation Research, 1997, pp. 567-574, vol. 81.

Yancopoulos, George D. et al., Vascular-specific growth factors and blood vessel formation, Nature, 2000, pp. 242-248, vol. 407.

Zweig, Mark H. and Campbell, Gregory, Receiver-Operating Characteristic (ROC) Plots: A Fundamental Evaluation Tool in Clinical Medicine, Clinical Chemistry, 1993, pp. 561-577, vol. 39, No. 4.

Song Haoming et al., Relationship between levels of IL-6, CRP, Ang II and atrial fibrillation in patients with chronic heat failure, Chinese Heart Journal, No. 04, Aug. 25, 2008 (English Abstract only).

Wang Mingyi, Effects of irbesartan and amlodipine on paroxysmal atrial fibrillation in elderly patients with hypertension, China Medical Herald, No. 17, Jun. 15, 2008 (English Abstract only).

Yu Jianhua, The change of plasma brain natriretic peptide angiotensin II in patients with atrial fibrillation and the intervention of losartan, Chin J Misdiagn, No. 14, May 15, 2008 (English Abstract only).

Zhang Haijun, Role of benazepril in preventing recurrence of atrial fibrillation after cardioversion, Chinese Medicine of Factory and Mine, No. 4, Aug. 30, 2006 (English Abstract only).

Zhang Weize et al., Effects of angiotensin II on atrial fibrosis and Cx40 remodeling in rats, Chinese Journal of Cardiac Pacing and Electrophysiology, No. 04, Aug. 25, 2007 (English Abstract only).

Zhao Hui et al., Intervention of losartan on serum brain natriuretic peptide and angiotensin II levels in patients with paroxysmal atrial fibrillation, Journal of Clinical Cardiology, No. 08, Aug. 25, 2008 (English Abstract only).

* cited by examiner

CIRCULATING ANGIOPOIETIN-2 (ANG-2) FOR THE PREDICTION OF RECURRENCE OF ATRIAL FIBRILLATION

CROSS-REFERENCE TO RELATED APPLICATIONS

This application is a continuation of International Application No. PC/EP2017/064970 filed Jun. 19, 2017, which claims priority to European Application No. 16174910.6 filed Jun. 17, 2016, the disclosures of which are incorporated by reference in their entirety.

SUMMARY OF THE INVENTION

The present invention relates to a method for predicting the risk of recurrence of Atrial Fibrillation in a subject based on determining the amount of the biomarker Angiopoietin-2 (Ang-2) and optionally of at least one further biomarker in a sample from the subject. The present invention also contemplates a method of diagnosing Atrial Fibrillation in a subject suspected to suffer from Atrial Fibrillation based on determining the amount of the biomarker Angiopoietin-2 (Ang-2) and optionally of at least one further biomarker in a sample from the subject. Further envisaged are devices adapted to carry out the method of the present invention.

BACKGROUND OF THE INVENTION

The present invention relates to a method for predicting the risk of recurrence of Atrial Fibrillation in a subject based on determining the amount of the biomarker Angiopoietin-2 (Ang-2) and optionally of at least one further biomarker in a sample from the subject. The present invention also contemplates a method of diagnosing Atrial Fibrillation in a subject suspected to suffer from Atrial Fibrillation based on determining the amount of the biomarker Angiopoietin-2 (Ang-2) and optionally of at least one further biomarker in a sample from the subject. Further envisaged are devices adapted to carry out the method of the present invention.

Atrial fibrillation (AF) is the most common type of heart arrhythmia and one of the most wide-spread conditions among the elderly population. Atrial fibrillation is characterized by irregular heart beating and often starts with brief periods of abnormal beating that can increase over time and may become a permanent condition. An estimated 2.7-6.1 million people in the United States have Atrial Fibrillation and approximately 33 million people globally (Chugh S S. et al, Circulation 2014; 129:837-47). Patients with AF have a higher stroke rate, and are at higher risk of developing congestive heart failure as compared to patients in sinus rhythm.

Angiopoietins are glycoproteins that are involved in angiogenesis. Because they are also expressed in healthy tissue, they are supposed to stabilize existing vessels and modulating the interaction between endothelial cells and surrounding vascular smooth muscle cells (Wong A L, et al. Circ Res. 1997; 81:567-74). Four angiopoietins are known, angiopoietin-1 (Ang-1) to angiopoietin-4 (Ang-4). Human angiopoietin-2 (Ang-2) is e.g. described in Maisonpierre P C et al. (Science 277 (1997) 55-60 and Cheung, A. H., et al, Genomics 48 (1998) 389-91) and is one of four members of the angiopoietin family. Ang-2 was discovered as ligand for the Ties, a family of tyrosine kinases that is selectively expressed within the vascular endothelium (Yancopoulos, G. D., et al., Nature 407 (2000) 242-48).

While Ang-1 is an agonist of the endothelial cell-specific Tie2 receptor tyrosine kinase and has pro-angiogenetic properties, it was found that Ang-2 disrupts blood vessel formation and has antagonistic signaling action through the Tie-2 receptor (Maisonpierre P C et al., Science 1997; 277:55-60)

Angiopoietin-2 (Ang-2) is known to impair endothelial integrity and has been shown elevated in heart failure (see e.g. Poss et al. Angiopoietin-2 and outcome in patients with acute decompensated heart failure. Clin Res Cardiol. May 2015; 104(5):380-387, or Lukasz et al. Angiopoietin-2 in adults with congenital heart disease and heart failure. PLoS One. 2013; 8(6) e66861).

Ang-2 has been found to be elevated in patients with chronic (permanent) Atrial Fibrillation (Freestone et al., Angiogenic factors in Atrial Fibrillation: a possible role in thrombogenesis? Ann Med 2005; 37: 365-72 or Choudhury et al., Relationship of Soluble CD40 Ligand to Vascular Endothelial Growth Factor, Angiopoietins, and Tissue Factor in Atrial Fibrillation, CHEST 2007; 132:1913-1919), whereas Ang-1 has not found to be influenced by atrial fibrillation in these 2 studies. The rate of progression and risk factors for progression from paroxysmal and persistent to permanent atrial fibrillation are clinically poorly understood (Kerr C R et al., Am Heart J. 2005; 149:489-496).

Latini (J Intern Med. 2011 February; 269(2):160-71) discloses a method for predicting recurrence of atrial fibrillation based on the detection of NTproANP, hsTnT or NTproBNP in patients with a history of AF.

Masson (Cardiovasc Drugs Ther 2015; 29:551) discloses the beneficial use of cardiac biomarkers for prediction of recurrent atrial fibrillation versus a variety of analyzed vasoactive or inflammatory biomarkers in samples of the GISSI AF biomarker substudy. It is concluded, that predicting the risk of recurrence of AF in a patient in sinus rhythm through echocardiography and assays of circulating biomarkers is a completely different and much more challenging task than showing expected alterations of the same variables when AF in ongoing.

Masson (Heart 2010; 96: 1909-1914) discloses the prediction of recurrence of atrial fibrillation based on the determination of inflammatory markers such as IL-6 Inflammatory markers would be increased, but would be weak predictors for first recurrence of AF.

WO 2014/072500 discloses means and methods for diagnosing a recent paroxysmal Atrial Fibrillation in a subject, comprising determining the amount of at least one marker selected from the group consisting of e.g. a cardiac Troponin, a BNP-type peptide, and IGFBP-7 (Insulin like growth factor binding protein 7) and Interleukin-6 (IL-6) in a sample from the subject.

Up to now, angiopoietin-2 was observed only in association with permanent Atrial Fibrillation. However, predicting the risk of recurrence of AF in a patient currently in sinus rhythm through electrocardiogram and/or assays of circulating biomarkers is a completely different and much more challenging task than showing expected alterations of the same variables when AF is ongoing (Masson et al. Cardiovasc Drugs Ther (2015) 29:551). Angiopoietin-2 was not yet used to predict the recurrence of Atrial Fibrillation in patients having had already Atrial Fibrillation and mostly paroxysmal AF. Nevertheless, prediction of the recurrence of Atrial Fibrillation, appropriate selection of preventive medication and prediction of therapy success are important clinical unmet needs. Advantageously, it has been shown in the studies underlying the present invention that Angiopoietin-2 either alone or in combination with at least one further biomarker selected from the group consisting of Angiopoietin-1 (Ang-1), a BNP-type peptide, CK-MB (Muscle-Brain type Creatine Kinase), and IGFBP-7 (Insulin-like Growth Factor Binding Protein 7) and a cardiac Troponin allows for a reliable prediction of recurrence of Atrial Fibrillation (see Examples). Thanks to the findings of the present invention, a patient can be identified and treated according to the risk.

DETAILED DESCRIPTION OF THE INVENTION

Figure 1:
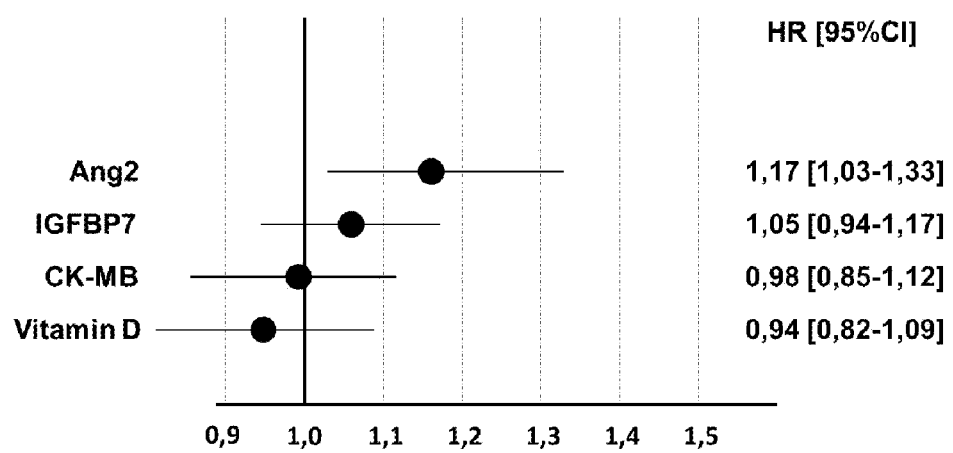
FIG. 1 shows: Cox multivariable models for first AF recurrence in GISSI-AF adjusted for peripheral artery disease, lone AF, smoking, heart rate, ≥2 episodes of AF in previous 6 months with/without cardioversion. Data shown as hazard ratio (HR) for an increment of 1 SD of baseline concentration of biomarkers.

The present invention relates, among other things, to a method for predicting the risk of recurrence of Atrial Fibrillation in a subject comprising the determination of the amount of the biomarker Angiopoietin-2 (Ang-2) and optionally the amount of at least one further biomarker selected from the group consisting of Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin in a sample from a subject.

In a preferred embodiment of the method of the present invention, the method further comprises the step of comparing the determined amount(s) of the biomarker(s) to a reference amount (or to reference amounts).

Accordingly, the present invention in particular concerns a method for predicting the risk of recurrence of Atrial Fibrillation in a subject, said method comprising the steps of
(a) determining the amount of the biomarker Angiopoietin-2 (Ang-2) and optionally the amount of at least one further biomarker selected from the group consisting of Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin in a sample from a subject, and
(b) comparing the amount(s) of the biomarker(s) as determined in step (a) to a reference amount (or to reference amounts).

Preferably, the prediction of recurrence of Atrial Fibrillation is based on the results of the comparison step (b). Thus, the method of the present invention can comprise the further step (c) of predicting the risk of recurrence of Atrial Fibrillation in the subject based on the results of step (b).

The method as referred to in accordance with the present invention includes a method which essentially consists of the aforementioned steps or a method which includes further steps. Moreover, the method of the present invention, preferably, is an ex vivo or in vitro method. Moreover, it may comprise steps in addition to those explicitly mentioned above. For example, further steps may relate to the determination of further markers and/or to sample pre-treatments or evaluation of the results obtained by the method. The method of the present invention may be also used for monitoring, confirmation, and sub-classification of the subject. The method may be carried out manually or assisted by automation. Preferably, step (a), (b) and/or (c) may in total or in part be assisted by automation, e.g., by a suitable robotic and sensory equipment for the determination in step (a) or a computer-implemented calculation in step (b).

The term "Atrial Fibrillation" is well known in the art. As used herein, the term preferably refers to a supraventricular tachyarrhythmia characterized by uncoordinated atrial activation with consequent deterioration of atrial mechanical function. In particular, the term refers to an abnormal heart rhythm characterized by rapid and irregular beating. It involves the two upper chambers of the heart. In a normal heart rhythm, the impulse generated by the sino-atrial node spreads through the heart and causes contraction of the heart muscle and pumping of blood. In Atrial Fibrillation, the regular electrical impulses of the sino-atrial node are replaced by disorganized, rapid electrical impulses which result in irregular heartbeats. Symptoms of Atrial Fibrillation are heart palpitations, fainting, shortness of breath, or chest pain. However, most episodes have no symptoms. On the electrocardiogram Atrial Fibrillation is characterized by the replacement of consistent P waves by rapid oscillations or fibrillatory waves that vary in amplitude, shape, and timing, associated with an irregular, frequently rapid ventricular response when atrioventricular conduction is intact.

The American College of Cardiology (ACC), American Heart Association (AHA), and the European Society of Cardiology (ESC) propose the following classification system (see Fuster (2006) Circulation 114 (7): e257-354 which herewith is incorporated by reference in its entirety, see e.g. FIG. 3 in the document): First detected AF, paroxysmal AF, persistent AF, and permanent AF.

All people with AF are initially in the category called first detected AF. However, the subject may or may not have had previous undetected episodes. A subject suffers from permanent AF, if the AF has persisted for more than one year. In particular, conversion back to sinus rhythm does not occur (or only with medical intervention). A subject suffers from persistent AF, if the AF lasts more than 7 days. The subject may require either pharmacologic or electrical intervention to terminate Atrial Fibrillation. Thus persistent AF occurs in episodes, but the arrhythmia does typically not convert back to sinus rhythm spontaneously (i.e. without medical intervention). Paroxysmal Atrial Fibrillation, preferably, refers to an intermittent episode of Atrial Fibrillation which lasts not longer than 7 days and terminates spontaneously (i.e. without medical intervention). In most cases of paroxysmal AF, the episodes last less than 24 hours. Thus, whereas paroxysmal atrial fibrillation terminates spontaneously, persistent atrial fibrillation does not end spontaneously and requires electrical or pharmacological cardioversion for termination, or other procedures, such as ablation procedures (Fuster (2006) Circulation 114 (7): e257-354).

In a preferred embodiment of the present invention, the term "paroxysmal atrial fibrillation" is defined as episodes of AF that terminate spontaneously in less than 48 hours, more preferably in less than 24 hours, and, most preferably in less than 12 hours. Both persistent and paroxysmal AF may be recurrent.

In accordance with the method the risk of recurrence of Atrial Fibrillation shall be predicted. Thus, it is to be understood that the subject to be tested is a subject who has suffered from Atrial Fibrillation before carrying out the method of the present invention. Thus, the subject shall have experienced episodes of Atrial Fibrillation previously. Accordingly, the subject preferably suffers from atrial fibrillation, in particular, from persistent or paroxysmal atrial fibrillation. Preferably, the subject suffering from atrial fibrillation had one or more episodes of atrial fibrillation within 6 months, more preferably, within one month, even more preferably within 14 days, and most preferably within seven days before obtaining the test sample. However, the subject preferably does not have an episode of atrial fibrillation at the time at which the sample to be tested is obtained. Thus, the subject preferably has a normal sinus rhythm at this time. Preferably, the subject did not experience an episode of atrial fibrillation within 48 hours before obtaining the test sample from the subject. Accordingly, it is envisaged that the last episode of atrial fibrillation terminated at least 48 hours before obtaining the test sample (either with or without medical intervention).

Preferably, the subject to be tested in accordance with the methods of the present invention does not suffer from permanent atrial fibrillation.

In preferred embodiments, at least some of the previous episodes of Atrial Fibrillation shall have been detected. Accordingly, it is envisaged that the subject to be tested has a known history of Atrial Fibrillation.

In a preferred embodiment, the subject has paroxysmal atrial fibrillation. Preferably, said subject having paroxysmal atrial fibrillation had one or more episodes of atrial fibrillation within 6 months, more preferably, within one month, even more preferably within 14 days, and most preferably within seven days before the sample to be tested is obtained. Said one or more episodes of atrial fibrillation, preferably terminated spontaneously, i.e. without medical intervention. Preferably, the last episode terminated spontaneously at least 48 hours before the sample to be tested is obtained.

In another preferred embodiment, the subject has persistent atrial fibrillation. Preferably, one or more of the previous episodes of Atrial Fibrillation did not end spontaneously. Thus, it is envisaged that the subject has been subjected to cardioversion, i.e. successful cardioversion. In particular, it is envisaged that the subject has been subjected to cardioversion within 14 days before the sample to be tested has been obtained (e.g. within 7 days before the sample has been obtained). Said cardioversion shall have been carried out in order to terminate the last diagnosed episode of Atrial Fibrillation. Cardioversion is a medical procedure by which cardiac arrhythmia is converted to a normal rhythm. This can be achieved by electrical cardioversion or cardioversion with an antiarrhythmic agent. Preferably, said cardioversion has been carried out at least 48 hours before obtaining the test sample.

In accordance with the present invention, it is contemplated that the subject does not experience episodes of Atrial Fibrillation when the sample is obtained. Thus, the subject shall have a normal sinus rhythm when the sample is obtained.

The "subject" as referred to herein is, preferably, a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Preferably, the subject is a human subject.

In accordance with the method of the present invention, the risk of recurrence of Atrial Fibrillation shall be predicted, and, thus, the risk of a subject to suffer from recurrent Atrial Fibrillation. Preferably, the risk of recurrence of AF within about three months, within about six months, or within about one year after carrying out the method of the present invention (or to be more precise after the sample has been obtained). In a preferred embodiment, the risk of recurrence of Atrial Fibrillation within about one year is predicted.

Preferably, the term "about" as used herein encompasses a range of + and −20% relative to the specific value, amount, concentration, level, etc., e.g., indication of a value of "about 100" is meant to encompass a value of a numerical range of 100+/−20%, i.e., a value range from 80 to 120. Preferably, the term encompasses a range of + and −10% relative to the specific value, amount, concentration, level, etc. and, more preferably, a range of + and −5% relative to the specific value, amount, concentration, level, etc. Most preferably, the term "about" refers to the exact value, amount, concentration, level, etc.

Preferably, term "predicting the risk" as used herein refers to assessing the probability according to which the subject will suffer from recurrence of Atrial Fibrillation. Typically, it is predicted whether a subject is at risk (and thus at elevated risk) or not at risk (and thus at reduced risk) of recurrence of Atrial Fibrillation. Accordingly, the method of the present invention allows for differentiating between a subject at risk and a subject not at risk of Atrial Fibrillation. Preferably, the term "predicting the risk" also encompasses aiding in the prediction of the risk such as aiding a physician in the prediction of the risk.

As set forth above, the risk/probability of recurrence of Atrial Fibrillation within a certain time window shall be predicted. In a preferred embodiment of the present invention, the predictive window is an interval of about three months, about six months, or about one year. Preferably, said predictive window is calculated from the completion of the method of the present invention. More preferably, said predictive window is calculated from the time point at which the sample to be tested has been obtained. As will be understood by those skilled in the art, the prediction of a risk is usually not intended to be correct for 100% of the subjects. The term, however, may require that prediction can be made for a statistically significant portion of subjects in a proper and correct manner. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98%, or at least 99%. The p-values are, preferably, 0.1, 0.05, 0.01, 0.005, or 0.0001.

In a preferred embodiment, the expression "predicting the risk of recurrence of Atrial Fibrillation" means that the subject to be analyzed by the method of the present invention is allocated either into the group of subjects being at risk of recurrence of Atrial Fibrillation, or into the group of subjects not being at risk of recurrence of Atrial Fibrillation. Thus, it is predicted whether the subject is at risk or not at risk of recurrence of Atrial Fibrillation. As used herein "a subject who is at risk recurrence of Atrial Fibrillation", preferably has an elevated risk of recurrence of Atrial Fibrillation (preferably within the predictive window). Preferably, said risk is elevated as compared to the average risk in a cohort of subjects. As used herein, "a subject who is not at risk of recurrence of Atrial Fibrillation", preferably, has a reduced risk of recurrence of Atrial Fibrillation (preferably within the predictive window). Preferably, said risk is reduced as compared to the average risk in a cohort of subjects. A subject who is at risk of recurrence of Atrial Fibrillation preferably has a risk or recurrence of at least 20% or more preferably of at least 30%, preferably, within a predictive window of about one year. Most preferably, the subject has a hazard ratio >1.1 for an increment of 1 SD of baseline concentration of biomarkers, preferably, within a predictive window of about one year. A subject who is at not at risk of recurrence of Atrial Fibrillation preferably has a risk of lower than 12%, more preferably of lower than 10% of recurrence of AF, preferably within a predictive window of one year. In an alternative embodiment, said subject has a hazard ratio of ≤1 for an increment of 1 SD of baseline concentration of biomarkers, preferably, within a predictive window of about one year.

The term "sample" refers to a sample of a body fluid, to a sample of separated cells or to a sample from a tissue or an organ. Samples of body fluids can be obtained by well-known techniques and include, samples of blood, plasma, serum, urine, lymphatic fluid, sputum, ascites, or any other bodily secretion or derivative thereof. Tissue or organ samples may be obtained from any tissue or organ by, e.g., biopsy. Separated cells may be obtained from the body fluids or the tissues or organs by separating techniques such as centrifugation or cell sorting. E.g., cell-, tissue- or organ samples may be obtained from those cells, tissues or organs which express or produce the biomarker. The sample may be frozen, fresh, fixed (e.g. formalin fixed), centrifuged, and/or embedded (e.g. paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the biomarker(s) in the sample.

In a preferred embodiment of the present invention, the sample is a blood (i.e. whole blood), serum or plasma sample. Serum is the liquid fraction of whole blood that is obtained after the blood is allowed to clot. For obtaining the serum, the clot is removed by centrifugation and the supernatant is collected. Plasma is the acellular fluid portion of blood. For obtaining a plasma sample, whole blood is collected in anticoagulant-treated tubes (e.g. citrate-treated or EDTA-treated tubes). Cells are removed from the sample by centrifugation and the supernatant (i.e. the plasma sample) is obtained.

The biomarker Angiopoietin-2 (abbreviated "Ang-2", frequently also referred to as ANGPT2) is well known in the art. It is a naturally occurring antagonist for both Ang-1 ( ) and TIE2 (see e.g. Maisonpierre et al., Science 277 (1997) 55-60). The protein can induce tyrosine phosphorylation of TEK/TIE2 in the absence of ANG-1. In the absence of angiogenic inducers, such as VEGF, ANG2-mediated loosening of cell-matrix contacts may induce endothelial cell apoptosis with consequent vascular regression. In concert with VEGF, it may facilitate endothelial cell migration and proliferation, thus serving as a permissive angiogenic signal. The sequence of human Angiopoietin is well known in the art. Uniprot lists three isoforms of Angiopoietin-2: Isoform 1 (Uniprot identifier: O15123-1), Isoform 2 (identifier: O15123-2) and Isoform 3 (O15123-3). In a preferred embodiment, the total amount of Angiopoietin-2 is determined. The total amount is preferably the sum of the amounts of complexed and free Angiopoietin-2.

In a preferred embodiment of the method of the present invention, the method further comprises the determination of the amount(s) of at least one further biomarker selected from the group consisting of Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin in a sample (in particular in the sample) from the subject.

The further biomarkers referred to the previous paragraph are well known in the art.

The biomarker angiopoietin 1 (Ang-1) is an angiopoietin which is encoded by the ANGPT1 gene. The sequence of human Ang-1 is well-known in the art and e.g. can be assessed via Uni-Prot (the database entry Q15389).

The Brain Natriuretic Peptide type peptide (herein also referred to as "BNP-type peptide") is preferably selected from the group consisting of pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP). Preferably, the BNP-type peptide according to the present invention is BNP or, in particular, NT-proBNP. BNP is the active hormone and has a shorter half-life than its respective inactive counterpart NT-proBNP.

IGFBP-7 (Insulin-like Growth Factor Binding Protein 7) is a 30-kDa modular glycoprotein known to be secreted by endothelial cells, vascular smooth muscle cells, fibroblasts, and epithelial cells (Ono, Y., et al., Biochem Biophys Res Comm 202 (1994) 1490-1496). Preferably, the term "IGFBP-7" refers to human IGFBP-7. The sequence of the protein is well-known in the art and is e.g. accessible via UniProt (Q16270, IBP7_HUMAN), or via GenBank (NP_001240764.1). A detailed definition of the biomarker IGFBP-7 is e.g. provided in WO 2008/089994 which herewith is incorporated by reference in its entirety. There are two isoforms of IGFBP-7, Isoform 1 and 2 which are produced by alternative splicing. In an embodiment of the present invention, the total amount of both isoforms is measured (for the sequence, see the UniProt database entry (Q16270-1 and Q16270-2).

The biomarker "CK-MB" (Muscle-Brain type Creatine Kinase, also referred to as "Creatine Kinase-MB", or "CPK-MB") is well known in the art. It is one the three isoenzymes of creatine kinase (CK) which is an enzyme expressed by various tissues and cell types (EC 2.7.3.2). The enzyme catalyses the conversion of creatine and uses adenosine triphosphate to generate phosphocreatine and adenosine diphosphate. Creatine kinases comprise two subunits which can be brain type (B) or muscle type (M) subunits. The isoenzyme CK-MB comprises a brain type and a muscle type subunit. The primary source of CK-MB is myocardial. However, it is also found in the skeletal muscle.

The term "cardiac Troponin" refers to all Troponin isoforms expressed in cells of the heart and, preferably, the subendocardial cells. These isoforms are well characterized in the art as described, e.g., in Anderson 1995, Circulation Research, vol. 76, no. 4: 681-686 and Ferrieres 1998, Clinical Chemistry, 44: 487-493. Preferably, the cardiac Troponin refers to Troponin T or Troponin I, and, more preferably, to Troponin T. The term does not encompass Troponin C. Amino acid sequences for human Troponin T and human Troponin I are disclosed in Anderson, Circ Res. 1995 April; 76(4):681-6 and Ferrieres 1998, Clinical Chemistry, 44: 487-493.

The present invention also contemplates to determine the amount of Ang-2 in combination with at least one additional biomarker. In an embodiment, the additional biomarker is Ang-1. In another embodiment, the at least one additional biomarker is a cardiac biomarker such as a BNP-type peptide and/or a cardiac Troponin. The additional determination of a cardiac biomarker allows to increase the specificity of the prediction or diagnosis of the present invention. Moreover, the additional determination of Ang-1 helps to increase the sensitivity. The sensitivity is increased by forming a ratio of opposingly acting and expressed biomarkers (e.g., Ang-1/Ang-2).

Preferred combinations of biomarker that can be determined in accordance with the methods and uses of the present invention are as follows:

Ang-2 and a BNP-type peptide, in particular NT-proBNP,
Ang-2 and a cardiac Troponin, in particular cTnT-hs (Troponin T high sensitive),
Ang-2 and Ang-1, or
Ang-2, a cardiac Troponin such as cTnT, a BNP-type peptide, in particular NT-proBNP.

A further preferred combination is Ang-2, Ang-1 and a BNP-type peptide such as NT-proBNP. Thus, the aforementioned amounts are determined. Further, it is envisaged to calculate a ratio of the amount of Ang-2 to the amount of Ang-1 and to compare the calculated ratio to a reference ratio. The amount of the BNP-type peptide is compared to a reference amount.

In a preferred embodiment of the method of the present invention, the further biomarker to be determined is Ang-1. Thus, the combined determination of the amount of the biomarker Angiopoietin-2 (Ang-2) and the amount of the biomarker Angiopoietin-1 (Ang-1) is envisaged. In a further step, the determined amounts of Ang-2 and Ang-1 are compared to reference amounts. Alternatively, it is envisaged to calculate a ratio of the amount of Angiopoietin-2 and the amount of Angiopoietin-1. In a subsequent step, said ratio is compared to a reference ratio.

Accordingly, the present invention is also concerned with a method for predicting the risk of recurrence of Atrial Fibrillation in a subject, said method comprising the steps of
(a) determining the amount of the biomarker Angiopoietin-2 (Ang-2) and the amount of the biomarker Angiopoietin-1 (Ang-1) in a sample from a subject, and
(b) calculating a ratio of the amount of Angiopoietin-2 and the amount of Angiopoietin-1, and
(c) comparing the calculated ratio to a reference ratio.

The prediction of recurrence of Atrial Fibrillation shall be based on the results of the comparison step (c). Thus, the method can comprise the further step (d) of predicting the risk of recurrence of Atrial Fibrillation in the subject based on the results of step (c).

The term "calculating a ratio" as referred to herein relates to calculating a ratio of the amount of Ang-2 and the amount of Ang-1 by dividing said amounts or by carrying out any other comparable mathematical calculation which puts into a relation the amount of Ang-2 towards the amount of Ang-1. In a preferred embodiment, the amount of Ang-2 is divided by the amount of Ang-1 in order to calculate the ratio (thus, the ratio of the amount of Ang-2 to the amount of Ang-1 is calculated). In another preferred embodiment, the amount of Ang-1 is divided by the amount of Ang-2 in order to calculate the ratio (thus, the ratio of the amount of Ang-1 to the amount of Ang-2 is calculated).

The term "determining" the amount of a biomarker as referred to herein refers to the quantification of the biomarker, e.g. to measuring the level of the biomarker in the sample, employing appropriate methods of detection described elsewhere herein. The terms "measuring" and "determining" are used herein interchangeably.

In an embodiment, the amount of a biomarker is measured by contacting the sample with an agent that specifically binds to the biomarker, thereby forming a complex between the agent and said biomarker, detecting the amount of complex formed, and thereby measuring the amount of said biomarker.

The biomarkers as referred to herein can be detected using methods generally known in the art. Methods of detection generally encompass methods to quantify the amount of a biomarker in the sample (quantitative method). It is generally known to the skilled artisan which of the following methods are suitable for qualitative and/or for quantitative detection of a biomarker. Samples can be conveniently assayed for, e.g., proteins using Westerns and immunoassays, like ELISAs, RI-As, fluorescence- and luminescence-based immunoassays, which are commercially available. Further suitable methods to detect biomarker include measuring a physical or chemical property specific for the peptide or polypeptide such as its precise molecular mass or NMR spectrum. Said methods comprise, e.g., biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

For the detection of biomarker proteins as referred to herein a wide range of immunoassay techniques using such an assay format are available, see, e.g., U.S. Pat. Nos. 4,016,043, 4,424,279, and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful immunoassays.

Methods employing electrochemiluminescent labels are well-known. Such methods make use of the ability of special metal complexes to achieve, by means of oxidation, an excited state from which they decay to ground state, emitting electrochemiluminescence. For review see Richter, M. M., Chem. Rev. 104 (2004) 3003-3036.

In an embodiment, the detection antibody (or an antigen-binding fragment thereof) to be used for measuring the amount of a biomarker is ruthenylated or iridinylated. Accordingly, the antibody (or an antigen-binding fragment thereof) shall comprise a ruthenium label. In an embodiment, said ruthenium label is a bipyridine-ruthenium(II) complex. Or the antibody (or an antigen-binding fragment thereof) shall comprise an iridium label. In an embodiment, said iridium label is a complex as disclosed in WO 2012/107419.

Measuring the amount of a polypeptide (such as Ang-2) may, preferably, comprise the steps of (a) contacting the polypeptide with an agent that specifically binds said polypeptide, (b) (optionally) removing non-bound agent, (c) measuring the amount of bound binding agent, i.e. the complex of the agent formed in step (a). According to a preferred embodiment, said steps of contacting, removing and measuring may be performed by an analyzer unit. According to some embodiments, said steps may be performed by a single analyzer unit of said system or by more than one analyzer unit in operable communication with each other. For example, according to a specific embodiment, said system disclosed herein may include a first analyzer unit for performing said steps of contacting and removing and a second analyzer unit, operably connected to said first analyzer unit by a transport unit (for example, a robotic arm), which performs said step of measuring.

The agent which specifically binds the biomarker (herein also referred to as "binding agent") may be coupled covalently or non-covalently to a label allowing detection and measurement of the bound agent. Labeling may be done by direct or indirect methods. Direct labeling involves coupling of the label directly (covalently or non-covalently) to the binding agent. Indirect labeling involves binding (covalently or non-covalently) of a secondary binding agent to the first binding agent. The secondary binding agent should specifically bind to the first binding agent. Said secondary binding agent may be coupled with a suitable label and/or be the target (receptor) of a tertiary binding agent binding to the secondary binding agent. Suitable secondary and higher order binding agents may include antibodies, secondary antibodies, and the well-known streptavidin-biotin system (Vector Laboratories, Inc.). The binding agent or substrate may also be "tagged" with one or more tags as known in the art. Such tags may then be targets for higher order binding agents. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium complexes, iridium complexes, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, avail-able as ready-made stock solution from Roche Diagnostics), CDP-Star™ (Amersham Bio-sciences), ECF™ (Amersham Biosciences). A suitable enzyme-substrate combination may result in a colored reaction product, fluorescence or chemo-luminescence, which can be measured according to methods known in the art (e.g. using a light-sensitive film or a suit-able camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. A radioactive label can be detected by any method known and appropriate, e.g. a light-sensitive film or a phosphor imager.

The amount of a polypeptide may be, also preferably, measured as follows: (a) contacting a solid support comprising a binding agent for the polypeptide as described elsewhere herein with a sample comprising the peptide or polypeptide and (b) measuring the amount of peptide or polypeptide which is bound to the support. Materials for manufacturing supports are well-known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc.

In yet an aspect the sample is removed from the complex formed between the binding agent and the at least one marker prior to the measurement of the amount of formed complex. Accordingly, in an aspect, the binding agent may be immobilized on a solid support. In yet an aspect, the sample can be removed from the formed complex on the solid support by applying a washing solution.

"Sandwich assays" are among the most useful and commonly used assays encompassing a number of variations of the sandwich assay technique. Briefly, in a typical assay, an unlabeled (capture) binding agent is immobilized or can be immobilized on a solid substrate, and the sample to be tested is brought into contact with the capture binding agent. After a suitable period of incubation, for a period of time sufficient to allow formation of a binding agent-biomarker complex, a second (detection) binding agent labeled with a reporter molecule capable of producing a detectable signal is then added and incubated, allowing time sufficient for the formation of another complex of binding agent-biomarker-labeled binding agent. Any unreacted material may be washed away, and the presence of the biomarker is determined by observation of a signal produced by the reporter molecule bound to the detection binding agent. The results may either be qualitative, by simple observation of a visible signal, or may be quantitated by comparison with a control sample containing known amounts of biomarker.

The incubation steps of a typical sandwich assays can be varied as required and appropriate. Such variations include for example simultaneous incubations, in which two or more of binding agent and biomarker are co-incubated. For example, both, the sample to be analyzed and a labeled binding agent are added simultaneously to an immobilized capture binding agent. It is also possible to first incubate the sample to be analyzed and a labeled binding agent and to thereafter add an antibody bound to a solid phase or capable of binding to a solid phase.

The formed complex between a specific binding agent and the biomarker shall be proportional to the amount of the biomarker present in the sample. It will be understood that the specificity and/or sensitivity of the binding agent to be applied defines the degree of proportion of at least one marker comprised in the sample which is capable of being specifically bound. Further details on how the measurement can be carried out are also found elsewhere herein. The amount of formed complex shall be transformed into an amount of the biomarker reflecting the amount indeed present in the sample.

The terms "binding agent", "specific binding agent", "analyte-specific binding agent", "detection agent" and "agent that specifically binds to a biomarker" are used interchangeably herein. Preferably it relates to an agent that comprises a binding moiety which specifically binds the corresponding biomarker. Examples of "binding agents" or "agents" are a nucleic acid probe, nucleic acid primer, DNA molecule, RNA molecule, aptamer, antibody, antibody fragment, peptide, peptide nucleic acid (PNA) or chemical compound. A preferred agent is an antibody which specifically binds to the biomarker to be measured. The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity (i.e. antigen-binding fragments thereof). Preferably, the antibody is a polyclonal antibody. More preferably, the antibody is a monoclonal antibody.

The term "specific binding" or "specifically bind" refers to a binding reaction wherein binding pair molecules exhibit a binding to each other under conditions where they do not significantly bind to other molecules. The term "specific binding" or "specifically binds", when referring to a protein or peptide as biomarker, refers to a binding reaction wherein a binding agent binds to the corresponding biomarker with an affinity of at least $10^{-7}$ M. The term "specific binding" or "specifically binds" preferably refers to an affinity of at least $10^{-8}$ M or even more preferred of at least $10^{-9}$ M for its target molecule. The term "specific" or "specifically" is used to indicate that other molecules present in the sample do not significantly bind to the binding agent specific for the target molecule.

The term "amount" as used herein encompasses the absolute amount of a biomarker as referred to herein, the relative amount or concentration of the said biomarker as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response amounts measured from biological read out systems in response to the peptides or intensity signals obtained from specifically bound ligands. It is to be understood that values correlating to the aforementioned amounts or parameters can also be obtained by all standard mathematical operations.

The term "comparing" as used herein refers to comparing the amount of the biomarker in the sample from the subject with the reference amount of the biomarker specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer-assisted. Thus, the comparison may be carried out by a computing device. The value of the measured or detected amount of the biomarker in the sample from the subject and the reference amount can be, e.g., compared to each other and the said comparison can be automatically carried out by a computer program executing an algorithm for the comparison. The computer program carrying out the said evaluation will provide the desired assessment in a suitable output format. For a computer-assisted comparison, the value of the measured amount may be compared to values corresponding to suitable references which are stored in a database by a computer program. The computer program may further evaluate the result of the comparison, i.e. automatically provide the desired assessment in a suitable output format. For a computer-assisted comparison, the value of the measured amount may be compared to values corresponding to suitable references which are stored in a database by a computer program. The computer program may further evaluate the result of the comparison, i.e. automatically provides the desired assessment in a suitable output format.

In accordance with the present invention the amount(s) of the biomarker(s) that is (are) determined shall be compared to a reference (or to references). The reference(s) is (are) preferably a reference amount (reference amounts). The term "reference amount" as used herein preferably refers to an amount which allows for allocation of a subject into either (i) the group of subjects being at risk of recurrence of Atrial Fibrillation or (ii) the group of subjects not being at risk of recurrence of Atrial Fibrillation. A suitable reference amount may be determined from a reference sample to be analyzed together, i.e. simultaneously or subsequently, with the test sample.

Reference amounts can, in principle, be calculated for a cohort of subjects as specified above based on the average or mean values for a given biomarker by applying standard methods of statistics. In particular, accuracy of a test such as a method aiming to diagnose an event, or not, is best described by its receiver-operating characteristics (ROC) (see especially Zweig 1993, Clin. Chem. 39:561-577). The ROC graph is a plot of all the sensitivity versus specificity pairs resulting from continuously varying the decision threshold over the entire range of data observed. The clinical performance of a diagnostic method depends on its accuracy, i.e. its ability to correctly allocate subjects to a certain prognosis or diagnosis. The ROC plot indicates the overlap between the two distributions by plotting the sensitivity versus 1—specificity for the complete range of thresholds suitable for making a distinction. On the y-axis is sensitivity, or the true-positive fraction, which is defined as the ratio of number of true-positive test results to the product of number of true-positive and number of false-negative test results. It is calculated solely from the affected subgroup. On the x-axis is the false-positive fraction, or 1—specificity, which is defined as the ratio of number of false-positive results to the product of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/1—specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis for a given event with a proper balance of sensitivity and specificity, respectively. Accordingly, the reference to be used for the aforementioned method of the present invention, i.e. a threshold which allows to differentiate between subjects being at risk of recurrence of Atrial Fibrillation or those not being at risk of recurrence of Atrial Fibrillation can be generated, preferably, by establishing a ROC for said cohort as described above and deriving a threshold amount therefrom. Dependent on a desired sensitivity and specificity for a diagnostic method, the ROC plot allows deriving a suitable threshold. It will be understood that an optimal sensitivity is desired for excluding a subject being at risk of recurrence of Atrial Fibrillation (i.e. a rule out) whereas an optimal specificity is envisaged for a subject to be assessed as being at risk of recurrence of Atrial Fibrillation (i.e. a rule in). In an embodiment, the method of the present invention allows for the prediction that a subject is at risk of recurrence of Atrial Fibrillation. Preferably, the subject is at risk, if the amount of Ang-2 (optionally the amount(s) of the at least one further biomarker(s)) is (are) above the reference amount(s). In an alternative embodiment, the method of the present invention allows for the prediction that a subject is not at risk of recurrence of Atrial Fibrillation. Preferably, the subject is at no risk, if the amount of Ang-2 (optionally the amount(s) of the at least one further biomarker(s)) is (are) below the reference amount(s)).

In a preferred embodiment, the term "reference amount" herein refers to a predetermined value. Said predetermined value shall allow for differentiating between a subject being at risk of recurrence of Atrial Fibrillation and a subject not being at risk of recurrence of Atrial Fibrillation.

Preferably, an amount of Ang-2 in the sample of the test subject above the reference amount indicates that the subject is at risk of recurrence of Atrial Fibrillation. Also preferably, an amount of Ang-2 in the sample below the reference amount indicates that the subject is not at risk of recurrence of Atrial Fibrillation.

An amount of Ang-2 in the sample of the test subject at the reference amount (i.e. essentially identical or equal to the reference amount), preferably also indicates that the subject is at risk of recurrence of Atrial Fibrillation.

In a preferred embodiment, the reference amount is derived from a subject or a group of subjects known to be at risk of recurrence of Atrial Fibrillation. In another preferred embodiment, the reference amount is derived from a subject or a group of subjects known not to be at risk of recurrence of Atrial Fibrillation.

If i) the reference amount is derived from a subject or a group of subjects known not to be at risk of recurrence of Atrial Fibrillation, an amount of the biomarker Ang-2 in the sample of the subject which is decreased as compared to the reference amount, is indicative for a subject who is not at risk of recurrence of Atrial Fibrillation.

If ii) the reference amount is derived from a subject or a group of subjects known to be at risk of recurrence of Atrial Fibrillation, an amount of the biomarker Ang-2 in the sample of the subject which is the same as the reference amount or which is increased as compared to the reference amount, is indicative for a subject who is at risk of recurrence of Atrial Fibrillation.

If the amount of more than one biomarker is determined (such as the amount of Ang-2 and the amount of a BNP-type peptide), it is envisaged that the individual amounts are compared to individual reference amounts (such as the amount of Ang-2 to a reference amount for Ang-2 and the amount of a BNP-type peptide to a reference amount for the BNP-type peptide).

Depending on whether the subject to be tested suffers from paroxysmal or persistent atrial fibrillation, different reference amounts or ratios may be applied for predicting the recurrence of atrial fibrillation. As will be understood by the skilled person, the reference amount or reference ratio for the prediction in a test subject who suffers from persistent atrial fibrillation will be higher than the reference amount or reference ratio for the prediction in a test subject who suffers from paroxysmal atrial fibrillation.

Preferably, amounts of the biomarkers in the sample of the test subject above (or at) the reference amounts indicate that the subject is at risk of recurrence of Atrial Fibrillation. Also preferably, amounts of the biomarkers in the sample below the reference amounts indicate that the subject is not at risk of recurrence of Atrial Fibrillation. This preferably applies to the biomarkers Angiopoietin-2 (Ang-2), a BNP-type peptide, CK-MB (Muscle-Brain type Creatine Kinase), IGFBP-7 (Insulin-like Growth Factor Binding Protein 7) and a cardiac Troponin. Thus, if e.g. the amounts of Ang-2 and a BNP-type peptide are determined, amounts of both biomarkers which are increased as compared to the reference amounts (or which are at or above the reference amounts) indicate that the subject is at risk of recurrence of Atrial Fibrillation, whereas amounts of both biomarkers which are decreased as compared to the reference amounts indicate that the subject is not at risk of recurrence of Atrial Fibrillation.

In contrast to the biomarkers as referred to above, a decreased amount of Ang-1 as compared to the reference amount indicates that the subject is at risk of recurrence of Atrial Fibrillation, whereas an essentially identical amount or an increased amount of Ang-1 as compared to the reference amount indicates that the subject is not at risk of recurrence of Atrial Fibrillation. Thus, an increased amount of Ang-2 (as compared to the reference amount for Ang-2) in combination with a decreased amount of Ang-1 (as compared to the reference amount for Ang-1) indicates that the subject is at risk of recurrence of Atrial Fibrillation, whereas a decreased amount of Ang-2 (as compared to the reference amount for Ang-2) in combination with an essentially identical amount or an increased amount of Ang-1 (as compared to the reference amount for Ang-1) indicates that the subject is not at risk of recurrence of Atrial Fibrillation As set forth above, the present invention may also encompass the calculation of ratio of the amount of Ang-2 and the amount of Ang-1 (i.e. of the amount of Ang-2 and the amount of Ang-1). Said ratio shall be compared to a reference ratio. Preferably, the reference ratio shall allow for differentiating between subjects being at risk of recurrence of AF and subjects not being at risk of recurrence of AF.

In an embodiment, the ratio of Ang-2 to Ang-1 is calculated. Thus, the reference ratio shall be a reference ratio of Ang-2 to Ang-1. Preferably, a ratio of Ang-2 to Ang-1 above the reference ratio is indicative for a subject who is at risk of recurrence of AF. Also preferably, a ratio of Ang-2 to Ang-1 below the reference ratio is indicative for a subject who is not at risk of recurrence of AF.

In an embodiment of the method of the invention, said method further comprises a step of recommending and/or initiating a suitable therapy based on the results of the prediction. Preferably, a suitable therapy is recommended or initiated if it is predicted that the subject is at risk of recurrence of AF. The suitable therapy can be any therapy that aims to reduce the risk of recurrence of atrial fibrillation. Preferably, said therapy is selected from the group consisting of administration of at least one anticoagulant, rhythm control and ablation. Said therapies are well known in the art and are e.g. reviewed in Fuster V et al. Circulation 2011; 123:e269-e367 which herewith is incorporated by reference in its entirety.

In an embodiment, the therapy is the administration of at least one anticoagulant. The administration of at least one anticoagulant shall aim to reduce or prevent coagulation of blood and related stroke. In an embodiment, at least one anticoagulant is selected from the group consisting of heparin, a coumarin derivative, such as warfarin or dicumarol, tissue factor pathway inhibitor (TFPI), antithrombin III, factor IXa inhibitors, factor Xa inhibitors, inhibitors of factors Va and VIIa and thrombin inhibitors.

The definitions given herein above apply mutatis mutandis to the following embodiments of the present invention.

The present invention is further concerned with a method for diagnosing Atrial Fibrillation in a subject, said method comprising the determination of the amount of the biomarker Angiopoietin-2 (Ang-2) and optionally the amount of at least one further biomarker selected from the group consisting of Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin in a sample from a subject.

The terms "sample", "subject", "comparing", "amount" etc. have been defined above. The definitions apply accordingly.

In a preferred embodiment of the aforementioned method of the present invention, the method further comprises the step of comparing the determined amount(s) of the biomarker(s) to a reference amount (or to reference amounts).

Accordingly, the present invention in particular concerns a method for diagnosing Atrial Fibrillation in a subject, said method comprising the steps of
  (a) determining the amount of the biomarker Angiopoietin-2 (Ang-2) and optionally the amount of at least one further biomarker selected from the group consisting of Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin in a sample from a subject, and
  (b) comparing the amount(s) of the biomarker(s) as determined in step (a) to a reference amount (or to reference amounts).

Preferably, the diagnosis of Atrial Fibrillation is based on the results of the comparison step (b). Thus, the method of the present invention can comprise the further step (c) diagnosing Atrial Fibrillation in the subject based on the results of step (b).

The subject to be tested according to the aforementioned method shall be a subject suspected to suffer from Atrial Fibrillation. Preferably, said subject is older than 70 years of age. Preferably, a subject who is suspected to suffer from AF, shall have shown symptoms of AF prior to carrying out the method for diagnosing AF. Said symptoms are usually transient and may arise in a few seconds and may disappear just as quickly. Symptoms of atrial fibrillation include dizziness, fainting, shortness of breath and, in particular, heart palpitations. As set forth elsewhere herein, it is contemplated that the subject does not experience episodes of Atrial Fibrillation when the sample is obtained. Thus, the subject shall have a normal sinus rhythm when the sample is obtained. Thus, the subject shall be at sinus rhythm.

Preferably, the term "diagnosing" as used herein means assessing whether a subject as referred to in accordance with the method of the present invention suffers from atrial fibrillation (AF), or not. In an embodiment, it is diagnosed that a subject suffers from AF. In an alternative embodiment, it is diagnosed that a subject does not suffer from AF.

In an embodiment of the method of the present invention, the atrial fibrillation to be diagnosed is paroxysmal atrial fibrillation. If the atrial fibrillation to be diagnosed is paroxysmal atrial fibrillation, it is envisaged that the subject to be tested does not suffer from persistent AF. Further, it is envisaged that the subject to be tested does not suffer from permanent AF. In particular, the subject shall be known not to suffer from persistent and permanent AF.

In another embodiment of the method of the present invention, the atrial fibrillation to be diagnosed is persistent atrial fibrillation.

As will be understood by those skilled in the art, the diagnosis described herein is usually not intended to be correct for all (i.e. 100%) of the subjects to be diagnosed. The term, however, requires that a statistically significant portion of subjects can be correctly diagnosed (e.g., a cohort in a cohort study). Thus, the actual diagnosis whether a subject suffers from AF, or not may comprise further steps such as the confirmation of a diagnosis. Thus, the diagnosis in the context of the present invention will aid the physician to assess whether a subject suffers from Atrial Fibrillation, or not. Accordingly, the term "diagnosing" in the context of the present invention preferably encompasses aiding the physician to assess whether a subject suffers from atrial fibrillation, or not.

Whether a portion is statistically significant can be determined without further ado by the person skilled in the art using various well-known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. More preferably, at least 60%, at least 70%, at least 80% or at least 90% of the subjects of a population can be properly diagnosed by the method of the present invention.

In accordance with the aforementioned method the biomarker(s) that is (are) determined shall be compared to a reference (or to references). The reference(s) is (are) preferably a reference amount (reference amounts). The term "reference amount" as used in connection with the aforementioned method preferably refers to an amount which allows for allocation of a subject into either (i) the group of subjects of suffering from Atrial Fibrillation or (ii) the group of not suffering Atrial Fibrillation. A suitable reference amount may be determined from a reference sample to be analyzed together, i.e. simultaneously or subsequently, with the test sample.

Reference amounts can be determined as described above. Accordingly, the reference to be used for the aforementioned method of the present invention, i.e. a threshold which helps to differentiate between subjects suffering from Atrial Fibrillation or those not suffering from AF can be generated, preferably, by establishing a ROC curve. Dependent on a desired sensitivity and specificity for a diagnostic method, the ROC plot allows deriving a suitable threshold. It will be understood that an optimal sensitivity is desired for excluding a subject being at risk of recurrence of Atrial Fibrillation (i.e. a rule out) whereas an optimal specificity is envisaged for a subject to be assessed as suffering from Atrial Fibrillation (i.e. a rule in). In an embodiment, the method of the present invention allows for the diagnosis as not suffering from Atrial Fibrillation. Preferably, the subject is suffering from AF, if the amount of Ang-2 (optionally the amount(s) of the at least one further biomarker(s)) is (are) above the reference amount(s). In an alternative embodiment, the method of the present invention allows for the diagnosis that a subject is not suffering from Atrial Fibrillation. Preferably, the subject is not suffering from AF, if the amount of Ang-2 (optionally the amount(s) of the at least one further biomarker(s)) is (are) below the reference amount(s).

In a preferred embodiment, the term "reference amount" herein refers to a predetermined value.

Said predetermined value shall allow for differentiating between a subject suffering from Atrial Fibrillation and a subject not suffering from Atrial Fibrillation.

Preferably, an amount of Ang-2 (and optionally of the further biomarkers as set forth above, in particular, a BNP-type peptide, CK-MB (Muscle-Brain type Creatine Kinase), IGFBP-7 (Insulin-like Growth Factor Binding Protein 7) and a cardiac Troponin) in the sample of the test subject at or above the reference amount indicates that the subject is suffering from AF. Also preferably, an amount of Ang-2 (and optionally of the further markers as set forth above, in particular a BNP-type peptide, CK-MB (Muscle-Brain type Creatine Kinase), IGFBP-7 (Insulin-like Growth Factor Binding Protein 7) and a cardiac Troponin) in the sample below the reference amount indicates that the subject is not suffering from Atrial Fibrillation.

The following diagnostic algorithm applies if the at least one further biomarker is Ang-1. This marker is decreased in subjects suffering from AF. Accordingly, the subject is preferably suffering from AF, if the amount of Ang-2 is above the reference amount for this marker (i.e. Ang-2) and if the amount of Ang-1 is below the reference amount for this marker. Accordingly, the subject is preferably not suffering from AF, if the amount of Ang-2 is equal or below the reference amount for this marker (i.e. Ang-2) and if the amount of Ang-1 is equal to or above the reference amount for this marker (i.e. Ang-1).

Preferred marker combinations are disclosed herein above in connection with the method for predicting the risk of recurrence of AF.

In a preferred embodiment of the aforementioned method, the further biomarker to be determined is Ang-1. Thus, the combined determination of the amount of the biomarker Angiopoietin-2 (Ang-2) and the amount of the biomarker Angiopoietin-1 (Ang-1) is envisaged. In a further step, the determined amounts of Ang-2 and Ang-1 are compared to reference amounts. Alternatively, it is envisaged to calculate a ratio of the amount of Angiopoietin-2 and the amount of Angiopoietin-1. In a subsequent step, said ratio is compared to a reference ratio. Based on this comparison step, it is diagnosed whether the subject suffers from AF or not. Preferably, a ratio of Ang-2 to Ang-1 above the reference ratio is indicative for a subject who suffers from AF. Also preferably, a ratio of Ang-2 to Ang-1 below the reference ratio is indicative for a subject who does not suffer from AF.

The present invention further relates to a method for monitoring a therapy that aims to reduce the risk of recurrence of atrial fibrillation, said method comprising:
(a) determining the amount of the biomarker Angiopoietin-2 (Ang-2) and optionally the amount of at least one further biomarker selected from the group consisting of Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin in a first sample from a subject,
(b) determining the amount(s) of the biomarker(s) as determined in step (a) in a second sample from a subject, and
(c) comparing the amount(s) of the biomarker(s) as determined in the first sample to the amount(s) of said biomarker(s) in said second sample.

The terms "sample", "subject", "comparing", "amount" etc. have been defined above in connection with the method of predicting the risk of recurrence of AF. The definitions apply accordingly.

The term "monitoring" as used herein, preferably, relates to assessing the effects a therapy as referred to herein. Thus, the aforementioned method may comprise the further step of monitoring the therapy based on the results of the comparison step carried out in step c). As will be understood by those skilled in the art, the prediction of a risk is usually not intended to be correct for 100% of the subjects. The term, however, requires that prediction can be made for a statistically significant portion of subjects in a proper and correct manner. Thus, the actual monitoring, may comprise further steps such as the confirmation.

Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98%, or at least 99%. The p-values are, preferably, 0.1, 0.05, 0.01, 0.005, or 0.0001.

The method as referred to above includes a method which essentially consists of the aforementioned steps or a method which includes further steps. Moreover, the method of the present invention, preferably, is an ex vivo or in vitro method. Moreover, it may comprise steps in addition to those explicitly mentioned above. For example, further steps may relate to the determination of further markers or to sample pre-treatments or evaluation of the results obtained by the method.

Preferably, by carrying out the method of the present invention it can be assessed whether the subject responds to said therapy or not. A subject responds to a therapy if the condition the subject improved between obtaining the first and the second sample. Preferably, a subject does not respond to the therapy if the condition worsened between obtaining the first and the second sample.

Preferably, the first sample is obtained prior to the initiation of said therapy. More preferably, the sample is obtained within one week in particular within two weeks prior to the initiation of said therapy Since the aforementioned method of the present invention comprises the assessment of changes of the amounts of biomarkers that are caused by the therapy as referred herein, the first sample may also be obtained after the initiation of said therapy (but before the second sample is obtained).

Thus, the second sample shall be obtained after the first sample. It is to be understood that the second sample shall be obtained after the initiation of said therapy.

Moreover, it is particularly contemplated that the second sample is obtained after a reasonable period of time after obtaining the first sample. It is to be understood, that the amounts of biomarkers referred herein, do not instantly change (e.g. within 1 minute or 1 hour) Therefore, "reasonable" in this context refers to intervals between obtaining the first and second sample which intervals allow the biomarker(s) to adjust. Therefore, the second sample, preferably, is obtained at least one month after said first sample, at least three months, or, in particular, at least six months after said first sample.

The following preferably applies to the biomarkers Angiopoietin-2 (Ang-2), a BNP-type peptide, CK-MB (Muscle-Brain type Creatine Kinase), IGFBP-7 (Insulin-like Growth Factor Binding Protein).

Preferably, an increase and, more preferably, a significant increase, and, most preferably, a statistically significant increase of the amount(s) of the biomarker(s) in the second sample as compared to the amount(s) of the biomarker(s) in the first sample is indicative for a subject who does not respond to the therapy. Also, an unchanged the amount(s) of the biomarker(s) in the second sample as compared to the amount(s) of the biomarker(s) in the first sample is preferably indicative for a subject who does not respond to the therapy. Also preferably, a decrease, more preferably, a significant decrease, most preferably, a statistically significant decrease of the amount(s) of the biomarker(s) in the second sample as compared to the amount(s) of the biomarker(s) in the first sample is indicative for a subject who responds to the therapy.

The following preferably applies to the biomarker Angiopoietin-1 (Ang-1):

Preferably, an unchanged (equal) amount or an increased amount of the biomarker Ang-1 in the second sample as compared to the amount of the biomarker in the first sample is indicative for a subject who responds to the therapy. Also preferably, a decrease, more preferably, a significant decrease, most preferably, a statistically significant decrease of the amount of the biomarker in the second sample as compared to the amount of the biomarker in the first sample is indicative for a subject who does not respond to the therapy.

Thus, if Ang-1 and Ang-2 are determined, e.g. an unchanged amount or an increase of the amount of the biomarker Ang-2 in the second sample as compared to the amount of the biomarker in the first sample in combination with a decrease of the amount Ang-1 in the second sample as compared to the amount of the biomarker in the first sample is indicative for a subject who does not respond to the therapy (and vice versa).

A subject is considered to respond to the therapy, it the therapy reduces the risk of the subject of recurrence of atrial fibrillation. A subject is considered as not to respond to the therapy, if the therapy does not the risk of the subject of recurrence of atrial fibrillation.

The terms "significant" and "statistically significant" are known by the person skilled in the art. Thus, whether an increase or decrease is significant or statistically significant can be determined without further ado by the person skilled in the art using various well known statistic evaluation tools. For example, a significant increase or decrease is an increase or decrease of at least 10%, in particular of at least 20%.

Preferred biomarker combinations are disclosed elsewhere herein.

In a preferred embodiment of the aforementioned method, the further biomarker to be determined in the first and second sample is Ang-1. Thus, the combined determination of the amount of the biomarker Angiopoietin-2 (Ang-2) and the amount of the biomarker Angiopoietin-1 (Ang-1) is envisaged in a first and second sample. In a preferred embodiment, it is envisaged to i) calculate a ratio of the amount of Angiopoietin-2 in the first sample and the amount of Angiopoietin-1 in the first sample (thereby calculating a first ratio), and to ii) calculate a ratio of the amount of Angiopoietin-2 in the second sample and the amount of Angiopoietin-1 in the second sample (thereby calculating a second ratio). In a subsequent step, said first ratio (i.e. the ratio in the first sample) is compared to the second ratio (i.e. the ratio in the second sample). Based on this comparison step, the therapy is monitored. Preferably, a ratio of the amount of Ang-2 to the amount of Ang-1 in the second sample which is increased, in particular significantly increased, as compared to the ratio of the amount of Ang-2 to the amount of Ang-1 in the first sample is indicative for a subject who responds to the therapy. Also preferably, a ratio of the amount of Ang-2 to the amount of Ang-1 in the second sample which is decreased, in particular significantly decreased, as compared to the ratio of the amount of Ang-2 to the amount of Ang-1 in the first sample is indicative for a subject who does not respond to the therapy.

The definitions given herein above in connection with predicting the recurrence of AF and diagnosing AF preferably apply to the following embodiments of the present invention.

The present invention is further concerned with a method for grading Atrial Fibrillation in a subject, said method comprising the determination of the amount of the biomarker Angiopoietin-2 (Ang-2) and optionally the amount of at least one further biomarker selected from the group consisting of Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin in a sample from a subject.

In a preferred embodiment of the aforementioned method of the present invention, the method further comprises the step of comparing the determined amount(s) of the biomarker(s) to a reference amount (or to reference amounts).

Accordingly, the present invention in particular concerns a method for grading Atrial Fibrillation in a subject, said method comprising the steps of
  (a) determining the amount of the biomarker Angiopoietin-2 (Ang-2) and optionally the amount of at least one further biomarker selected from the group consisting of Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin in a sample from a subject, and
  (b) comparing the amount(s) of the biomarker(s) as determined in step (a) to a reference amount (or to reference amounts).

Preferably, the grading of Atrial Fibrillation is based on the results of the comparison step (b). Thus, the method of the present invention can comprise the further step (c) grading Atrial Fibrillation in the subject based on the results of step (b).

The subject to be tested according to the aforementioned method preferably suffers from Atrial Fibrillation. In particular, the subject preferably has been diagnosed to suffer from Atrial Fibrillation (before carrying out the aforementioned method of the present invention). Accordingly, the aforementioned method shall allow for a further classification of the subject.

Preferably, the subject to be tested by the method for grading AF does not suffer from permanent AF.

In an embodiment, the subject to be tested does not experience an episode of Atrial Fibrillation when the sample is obtained. Thus, the subject shall have a normal sinus rhythm when the sample is obtained (and thus is at sinus rhythm).

In another embodiment, the subject experiences an episode of Atrial Fibrillation when the sample is obtained. In this embodiment, the subject is not at sinus rhythm.

Preferably, the term "grading atrial fibrillation" as used herein means assessing the severity of atrial fibrillation in a subject. In particular, the term means assessing whether a subject as referred to in accordance with this method suffer from a mild form of atrial fibrillation or a severe form of atrial fibrillation. Thus, by carrying out the claimed method, it can be differentiated between a mild form and a severe form of AF. A mild form of AF is preferably paroxysmal AF. A severe form of AF is preferably persistent AF.

As will be understood by those skilled in the art, the grading described herein is usually not intended to be correct for all (i.e. 100%) of the subjects to be graded. Thus, the actual grading may comprise further steps such as the confirmation of a grading. Accordingly, the term "grading" in the context of the present invention preferably encompasses aiding the physician to assess whether a subject suffers from a mild or severe form of atrial fibrillation.

In accordance with the aforementioned method the biomarker(s) that is (are) determined shall be compared to a reference (or to references). The reference(s) is (are) preferably a reference amount (reference amounts). The term "reference amount" as used in connection with the aforementioned method preferably refers to an amount which allows for allocation of a subject into either (i) the group of subjects of suffering from mild form Atrial Fibrillation or (ii) the group of subjects suffering from a severe form of AF. It is to be understood that the reference to be applied in the aforementioned method may differ from the reference amount to be applied in the method for diagnosing AF or for predicting the recurrence of AF. This is taken into account by the skilled person.

Reference amounts can be determined as described above. Accordingly, the reference to be used for the aforementioned method of the present invention, i.e. a threshold which helps to differentiate between subjects suffering from a mild form of Atrial Fibrillation or those suffering from a severe form of AF can be generated, preferably, by establishing a ROC curve.

In a preferred embodiment, the term "reference amount" herein refers to a predetermined value. Said predetermined value shall allow for differentiating between a subject suffering from a mild form of Atrial Fibrillation and a subject suffering from a severe form Atrial Fibrillation.

It has been shown in the studies of the present invention that the amount of Ang-2 is increased in subjects suffering from a severe form of AF (persistent AF) as compared to the amount of Ang-2 in subjects suffering from a mild form of AF (paroxysmal AF, see FIG. 2). Therefore, the diagnostic algorithm is as follows:

Preferably, an amount of Ang-2 (and optionally of the further biomarkers as set forth above, in particular, a BNP-type peptide, CK-MB (Muscle-Brain type Creatine Kinase), IGFBP-7 (Insulin-like Growth Factor Binding Protein 7) and a cardiac Troponin) in the sample of the test subject at or above the reference amount indicates that the subject is suffering from a severe form of AF. Also preferably, an amount of Ang-2 (and optionally of the further markers as set forth above, in particular a BNP-type peptide, CK-MB (Muscle-Brain type Creatine Kinase), IGFBP-7 (Insulin-like Growth Factor Binding Protein 7) and a cardiac Troponin) in the sample below the reference amount indicates that the subject is suffering from a mild form of AF.

The following diagnostic algorithm applies if the at least one further biomarker which is determined in addition to Ang-2 is Ang-1. Ang-1 is decreased in subjects suffering from a severe form of AF (as compared to subjects with a mild form of AF, see e.g. FIG. 2). Accordingly, the subject is preferably suffering from a severe form of AF, if the amount of Ang-2 is above the reference amount for this marker (i.e. Ang-2) and if the amount of Ang-1 is below the reference amount for this marker. Accordingly, the subject is preferably suffering from a mild form of AF, if the amount of Ang-2 is equal or below the reference amount for this marker (i.e. Ang-2) and if the amount of Ang-1 is equal to or above the reference amount for this marker (Ang-1).

Preferred marker combinations are disclosed herein above in connection with the method for predicting the risk of recurrence of AF.

In a preferred embodiment of the aforementioned method, the further biomarker to be determined is Ang-1. Thus, the combined determination of the amount of the biomarker Angiopoietin-2 (Ang-2) and the amount of the biomarker Angiopoietin-1 (Ang-1) is envisaged. In a further step, the determined amounts of Ang-2 and Ang-1 are compared to reference amounts. Alternatively, it is envisaged to calculate a ratio of the amount of Angiopoietin-2 and the amount of Angiopoietin-1. In a subsequent step, said ratio is compared to a reference ratio. Based on this comparison step, AF is graded. In particular, it is differentiated whether the subject suffers from a mild form AF or severe form of AF. Preferably, a ratio of Ang-2 to Ang-1 above the reference ratio is indicative for a subject who suffers from a severe from AF. Also preferably, a ratio of Ang-2 to Ang-1 below the reference ratio is indicative for a subject who suffers from a mild form of AF.

Further, the present invention concerns i) the use of the biomarker Angiopoietin-2 (Ang-2) and optionally of at least one further biomarker selected from the group consisting of Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin and/or ii) the use of an agent which specifically binds Angiopoietin-2 (Ang-2) and optionally of at least one further agent which specifically binds to a biomarker selected from Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin in a sample from a subject for predicting the risk of recurrence of Atrial Fibrillation.

Further, the present invention concerns i) the use of the biomarker Angiopoietin-2 (Ang-2) and optionally of at least one further biomarker selected from the group consisting of Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin and/or ii) the use of an agent which specifically binds Angiopoietin-2 (Ang-2) and optionally of at least one further agent which specifically binds to a biomarker selected from Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin in a sample from a subject for diagnosing atrial fibrillation.

Further, the present invention concerns i) the use of the biomarker Angiopoietin-2 (Ang-2) and optionally of at least one further biomarker selected from the group consisting of Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin and/or ii) the use of an agent which specifically binds Angiopoietin-2 (Ang-2) and optionally of at least one further agent which specifically binds to a biomarker selected from Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin in a first and second sample from a subject for monitoring a therapy that aims to reduce the risk of recurrence of atrial fibrillation.

Finally, the present invention concerns i) the use of the biomarker Angiopoietin-2 (Ang-2) and optionally of at least one further biomarker selected from the group consisting of Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin and/or ii) the use of an agent which specifically binds Angiopoietin-2 (Ang-2) and optionally of at least one further agent which specifically binds to a biomarker selected from Angiopoietin-1 (Ang-1), a BNP-type peptide, CK-MB (Muscle-Brain type Creatine Kinase), IGFBP-7 (Insulin-like Growth Factor Binding Protein 7) and a cardiac Troponin in a sample from a subject for grading Atrial Fibrillation.

The definitions and explanations given in connection with the methods of the present invention also apply to the uses of the present invention (e.g., see the definitions for the term "sample", "subject", "agent", etc. as provided elsewhere herein).

All references cited in this specification are herewith incorporated by reference with respect to their entire disclosure content and the disclosure content specifically mentioned in this specification.

EXAMPLES

The invention will be merely illustrated by the following Examples. The said Examples shall, whatsoever, not be construed in a manner limiting the scope of the invention.

Example 1

GISSI-AF Trial

The GISSI-AF trial was a double-blinded, randomized, placebo-controlled, multicenter trial that had enrolled 1442 patients in sinus rhythm with a known history of Atrial Fibrillation, mostly paroxysmal AF, documented by at least two or more episodes of symptomatic ECG-documented Atrial Fibrillation in the previous 6 months or successful electrical or pharmacologic cardioversion between 14 days and 48 h before randomization, and followed them for 12 months (Masson et al. 2015 Cardiovasc Drugs Ther 29:551)

The rationale, design, and results of the trial have already been published in detail earlier (ref: Disertori M, et al., J Cardiovasc Med. 2006; 7:29-38; ref Staszewsky L et al., Cardiovasc Drugs Ther 2015; 29:551-561) and under Clinical Trials.gov (with identifier NCT00376272).

All patients were age >40 years and had been on a stable treatment for Atrial Fibrillation and of any underlying cardiovascular disorder for at least 1 month before enrollment. Previously prescribed ACE inhibitors, beta-blockers and amiodarone for cardiovascular co-morbidities were permitted to be continued taking. Patients were randomized to receive valsartan or placebo The primary end points in the main trial were to assess the effect of the angiotensin II type 1 receptor blocker, valsartan, on (a) the time to first recurrence of Atrial Fibrillation and (b) the proportion of patients with more than one episode of Atrial Fibrillation in the 1-year observation period.

The biomarker substudy (N=382) comprised 203 subjects with and 179 controls without recurrent Atrial Fibrillation during the 12-month follow-up period (Masson S et al., Heart. 2010; 96:1909-14; Latini R et al, J Intern Med. 2011; 269:160-71). Blood samples were drawn at randomization and after 6 and 12 months of follow-up.

Example 2

Biomarker Measurements

Plasma concentrations of the biomarkers CK-MB, NT-proBNP, troponin T and Vitamin D were measured with the commercialized Elecsys® reagents from Roche Diagnostics (Mannheim, Germany). The biomarkers IGFBP7 and Ang-2 were measured with prototype Elecsys® reagents from Roche Diagnostics (Mannheim, Germany).

Ang-2-Assay using biotinylated MAB<Ang2>Bi and ruthenylated MAB<Ang2>F(ab')2-Ru:

An electrochemiluminescence immunoassay (ECLIA) for the specific measurement of Ang2 in particular in human serum or plasma samples was developed using the Elecsys® cobas analyzer e601. The Elecsys Ang2 immunoassay is an electrochemiluminescence immunoassay (ECLIA) that functions via the sandwich principle. There are two antibodies included in the assay, namely a biotinylated monoclonal antibody MAB<Ang2> (MAB<Ang2>Bi; capture antibody) and a ruthenylated F(ab')2-fragment of monoclonal anti-Ang2 antibody MAB<Ang2>(MAB<Ang2>F(ab')2-Ru; detection antibody), which form sandwich immunoassay complexes with Ang2 in the sample. The complexes are then bound to solid-phase streptavidin-coated microparticles. These are captured magnetically onto the electrode surface, leading to chemiluminescence emission upon application of voltage to the electrode, which is measured by a photomultiplier. Results are determined via an instrument-specific calibration curve determined by series of 6 calibrators with different concentrations of Ang2 across the measuring range. Samples are measured applying assay protocol 2 with pipetting volumes of 20 µl of the sample, 75 µl of reagent 1 (R1), 75 µl of reagent 2 (R2) and 30 µl of magnetic beads. R1 is containing 1.75 µg/ml MAB<Ang2>Bi in phosphate reaction buffer and reagent 2 (R2) is containing 1 µg/ml MAB<Ang2>F(ab')2-Ru in the same reaction buffer.

TABLE 1

Test characteristics

| Biomarker | Assay/Manufacturer | Unit | LOD | CV intra-assay (%) |
|---|---|---|---|---|
| IGFBP7 | ECLIA/RDG | ng/mL | 0.01 | 2 |
| Angiopoietin-2 | ECLIA/RDG | ng/mL | 0.042 | <6 |
| CK-MB | ECLIA/RDG | ng/mL | 0.3 | <4 |
| Vitamin D | ECLIA/RDG | ng/mL | 3 | <7.5 |
| Angiopoietin-1 | | ng/ml | 0.061 | 8.8 |

First results of the biomarker sub-study were previously published (Masson S et al., Heart. 2010; 96:1909-14; Latini R et al, J Intern Med. 2011; 269:160-71) where the cardiac biomarkers NT-proBNP or cTnT-hs were found to be elevated during episodes of AF and to be independently associated with first AF recurrence. Other markers cardiac markers (MR-proANP), vasoactive peptides (MR-proADM, CT-proET1, copeptin) and inflammatory biomarkers CRP-hs) were not predictive for recurrence of Atrial Fibrillation (Latini R et al, J Intern Med. 2011; 269:160-71)

Table 2 shows the results for IGFBP-7, Ang-2, CK-MB and Vit B for a 6-month follow-up of the GISSI AF study providing information, whether the blood biomarker is elevated in patients with recurrent AFib. Patients were in sinus rhythm (SR) at baseline.

TABLE 2

Biomarkers (Median, [Q1-Q3]) according to cardiac rhythm at 6-month follow-up

| Biomarker | SR (n = 284-294) | AF (n [32 [0 39-41]) | p |
|---|---|---|---|
| IGFBP7 (ng/mL) | 167 [153-186] | 186 [163-227] | 0.4 |
| Angiopoietin-2 (ng/mL) | 2.4 [2.0-3.0] | 3.3 [2.4-4.5] | 0.09 |
| CK-MB (ng/mL) | 2.4 [1.8-3.4] | 3.0 [2.2-3.9] | 0.89 |
| Vitamin D (ng/mL) | 14.6 [8.3-22.7] | 15.9 [6.9-24.4] | 0.21 |

Table 3 shows the results for IGFBP-7, Ang-2, CK-MB and Vit B for a 12-month follow-up.

TABLE 3

Biomarkers (Median, [Q1-Q3])
according to cardiac rhythm at 12-month follow-up

| Biomarker | SR (n = 273-282) | AF (n = 55-57) | p |
|---|---|---|---|
| IGFBP7 (ng/mL) | 172 [156-196] | 178 [159-214] | 0.1 |
| Angiopoietin-2 (ng/mL) | 2.4 [1.9-3.1] | 3.7 [2.8-4.9] | <.0001 |
| CK-MB (ng/mL) | 2.5 [1.8-3.5] | 2.7 [1.9-3.6] | 0.33 |
| Vitamin D (ng/mL) | 7.2 [5.1.11.6] | 7.9 [5.3-14.2] | 0.22 |

Thus, the markers are reliable predictors for the risk of recurrence of atrial fibrillation.

Example 3

Diagnosis of AF with the Ratio Ang-2:Ang-1

NTproBNP, Ang-2 and Ang-1 levels have been determined in plasma samples of n=56 patients with blood sampled and biomarkers assayed before open chest surgery because of CABG or valve surgery. Evidence of different types of AF, paroxysmal AF and persistent AF or SR (controls) was generated during surgery with simultaneous Endo-Epicardial High Density Activation Mapping. Patients with AF, paroxysmal AF or persistent AF and controls were matched with regard to gender, age and comorbidities.

Epicardial High Density Mapping is a different means for discrimination among subgroups of sinus rhythm, paroxysmal and persistent AF according to different conduction patterns of fibrillation waves resulting from electric activations (see Eckstein et al., Transmural Conduction Is the Predominant Mechanism of Breakthrough During Atrial Fibrillation Evidence From Simultaneous Endo-Epicardial High-Density Activation Mapping. Circ Arrhythm Electrophysiol. (2013) 6, pp. 334-341; van Marion et al., Diagnosis and Therapy of Atrial Fibrillation: the Past, the Present and the Future Diagnosis and Therapy of Atrial Fibrillation: the Past, the Present and the Future JAFIB: Journal of Atrial Fibrillation;Aug/Sep2015, Vol. 8 Issue 2, p 5).

Epicardial High Density Mapping e.g. allows for the diagnosis of paroxysmal atrial fibrillation even in the absence of an episode of Atrial Fibrillation. Thus, it allows for a reliable differentiation between subjects not suffering from AF, subjects suffering from paroxysmal AF and subjects suffering from persistent AF.

At the time of blood sampling
patients suffering from paroxysmal AF, optional in sinus rhythm; n=13 patients
persistent AF patients were not in sinus rhythm; n=15 patients
control patients were in sinus rhythm; n=28 patients.

Data evaluation showed that patients with Ang-2 levels above a reference value and Ang-1 levels below a reference value are suspected to have Atrial fibrillation and may benefit from anticoagulation. The observed AUC of Ang-2 for the detection of paroxysmal AF was 0.54 and for persistent AF 0.78. The observed AUC of Ang-1 for the detection of paroxysmal AF was 0.60 and for persistent AF 0.63. Thus, in the patients analyzed herein, the biomarker Ang-1 allows for an improved diagnosis of paroxysmal AF.

Figure 2A:
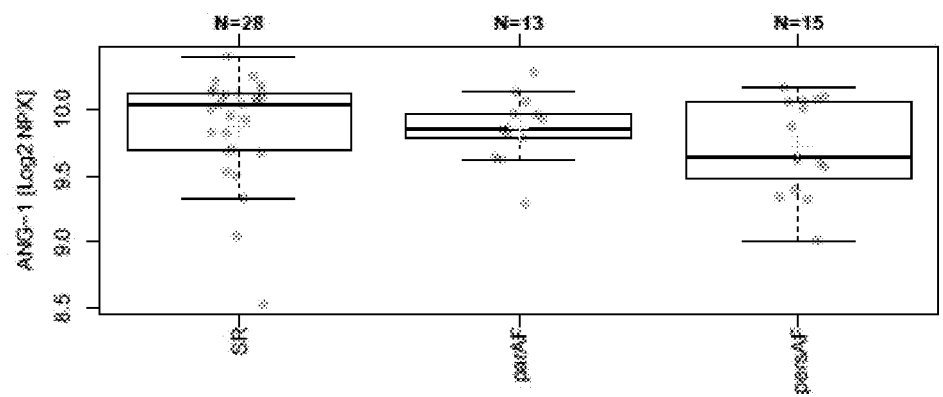
FIG. 2A shows: progressive decline of circulating Ang-1 levels could be detected from patients in sinus rhythm to paroxysmal AF patients to persistent AF patients.
Figure 2B:
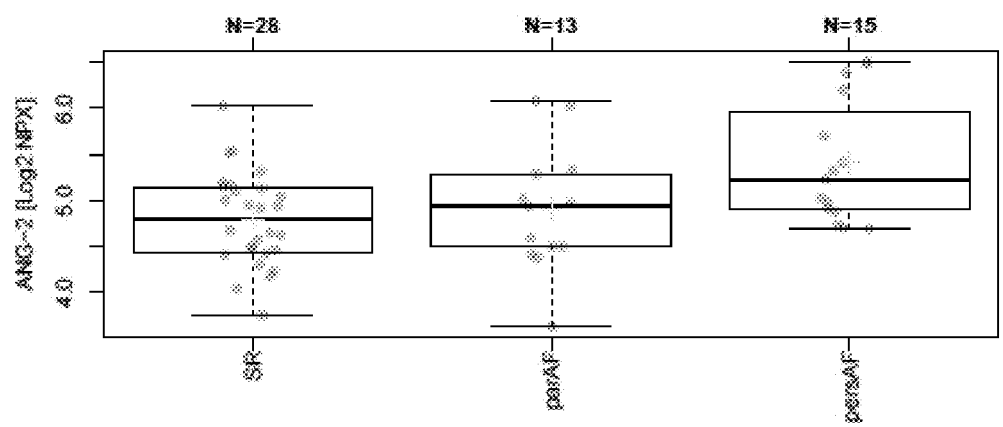
FIG. 2B shows: progressive increase of circulating Ang-2 levels could be detected from patients in sinus rhythm to paroxysmal AF patients to persistent AF patients.

As shown in FIG. 2b, a progressive increase of circulating Ang-2 levels could be detected from patients in sinus rhythm to paroxysmal AF patients to persistent AF patients. In contrast and as shown in FIG. 2a, a progressive decline of circulating Ang-1 levels could be detected from patients in sinus rhythm to paroxysmal AF patients to persistent AF patients. Thus, in the patients analyzed herein, the Ratio Ang-2 (upregulated)/Ang-1 (down-regulated) allows for an improved diagnosis of AF independent from other biomarkers.

TABLE 4

Ratio Ang-2:Ang-1

| Biomarker | AF AUC | Specificity at 60% Sensitivity | Sensitivity at 60% Specificity | p-value |
|---|---|---|---|---|
| Ang-1 | 0.629 | 57.1% | 0.607 | 0.100 |
| Ang-2 | 0.654 | 50.0% | 0.571 | 0.048 |
| Ratio Ang-2:Ang-1 | 0.680 | 67.9% | 0.679 | 0.020 |

| | paroxysm. AF AUC | Specificity at 60% Sensitivity | Sensitivity at 60% Specificity | p-value |
|---|---|---|---|---|
| Ang-1 | 0.596 | 57.1% | 61.5% | 0.338 |
| Ang-2 | 0.536 | 32.1% | 46.2% | 0.730 |
| Ratio Ang-2:Ang-1 | 0.459 | 32.1% | 30.8% | 0.688 |

| | persistent AF AUC | Specificity at 60% Sensitivity | Sensitivity at 60% Specificity | p-value |
|---|---|---|---|---|
| Ang-1 | 0.657 | 53.6% | 60.0% | 0.095 |
| Ang-2 | 0.757 | 60.7% | 66.7% | 0.005 |
| Ratio Ang-2:Ang-1 | 0.800 | 78.6% | 86.7% | 0.001 |

Table 4 summarizes the performance of biomarkers Ang-1 and Ang-2 alone and the Ratio Ang-2/Ang-1 in the 56 patients described in example 3.

As shown in table 4 the observed AUC of the Ratio Ang-2/Ang-1 was 0.680, with a sensitivity of 67.9% at 60% specificity for the detection of all subjects with Atrial Fibrillation (n=28) and a p-value of 0.02. The respective observed AUC for Ang-1 was 0.629 with a sensitivity of 60.7% at a specificity of 60% for the detection of Atrial Fibrillation in the 28 subjects versus 28 controls with a p-value of 0.1.

The respective observed AUC for Ang-2 was 0.654 with a sensitivity of 57.1% at a specificity of 60% for the detection of Atrial Fibrillation in the 28 subjects versus 28 controls with a respective p-value of 0.048. Thus, in conclusion both Ang-1 and/or Ang-2 were observed to be suited for the detection of paroxysmal and/or persistent AF. The proposed algorithm of the Ratio Ang-2:Ang-1 showed the best performance versus Ang-1 or Ang-2 in the detection of paroxysmal and/or persistent AF in the cohort analyzed herein. The observed sensitivities for detection of paroxysmal and or persistent AF at 60% specificity were 67.9%, 60.7% and 57.1% for the Ratio Ang-2:Ang-1, Ang-1 and Ang-2, respectively.

The observed AUC of the Ratio Ang-2:Ang-1 for the detection of paroxysmal AF was 0.459 with a sensitivity of 30.8% at a specificity of 60%. Ang-1 was detected in subjects with paroxysmal atrial fibrillation with a sensitivity of 61.5% at a specificity of 60% and a AUC of 0.596. Ang-2 was detected in the paroxysmal AF patients analyzed herein with a sensitivity of 46% at a specificity of 60% and a AUC of 0.536.

Thus, in conclusion Ang-1 showed a beneficial performance versus Ang-2 alone in the detection of paroxysmal AF in the analyzed patient cohort. The observed sensitivities for detection of paroxysmal AF at 60% specificity were 61.5%, 46.2% and 30.8% for Ang-1, Ang-2 and the Ratio Ang-2:Ang-1, respectively.

The observed AUC for the Ratio Ang-2:Ang-1 for the detection of persistent AF was 0.80 for the patients analyzed herein (86.7% sensitivity at 60% specificity, p-value 0.001). Ang-1 was detected in subjects with persistent atrial fibrillation with a sensitivity and specificity of 60% and a AUC of 0.657. The persistent AF patients were found with a AUC of 0.757 and a sensitivity of 66.7% at 60% specificity with Ang-2.

In conclusion, both biomarkers Ang-1 or Ang-2 were observed to be suited for the detection of persistent AF patients. With the ratio Ang-2:Ang-1 an improved performance in the detection of persistent AF could be achieved versus the use of any of both biomarkers, Ang-1 or Ang-2 alone. The observed sensitivities for detection of persistent AF at 60% specificity were 86.7%, 66.7% and 60.0% for the Ratio Ang-2:Ang-1, Ang-2 and Ang-1 respectively.

The observed AUC of NTproBNP for the detection of paroxysmal AF was 0.64 and for persistent AF 0.9 in the patients analyzed herein.

It is concluded, that the Ratio Ang-2 (upregulated)/Ang-1 (down-regulated) shows beneficial performance versus Ang-2 alone and may thus individually and/or in combination with NTproBNP assist in the detection of episodes of atrial fibrillation. Patients with Ang-2 levels above a reference value in combination with Ang-1 levels below a reference value are suspected to have Atrial fibrillation and may benefit from anticoagulation.

Thus, the diagnosis of Atrial Fibrillation in patients at risk may be achieved with the Ratio Ang-2/Ang-1 alone or in combination with NT-proBNP.

The invention claimed is:

1. A method of identifying a subject to be at risk of recurrence of Atrial Fibrillation, said method comprising:
   a) measuring an amount of Angiopoietin-2 (Ang-2) and optionally measuring an amount of at least one further biomarker selected from the group consisting of Angiopoietin-1 (Ang-1), BNP, NT-proBNP, CK-MB (Muscle-Brain type Creatine Kinase), IGFBP-7 (Insulin-like Growth Factor Binding Protein 7) and cardiac Troponin in a serum or plasma sample from a human subject who has a known history of atrial fibrillation, and who has normal sinus rhythm when the sample is obtained,
   b) comparing the measured amount of the Ang-2 in the subject to a reference amount of Ang-2 and optionally comparing the measured amount of the at least one further biomarker to a reference amount of the at least one further biomarker,
   c) identifying the subject to be at risk of recurrence of atrial fibrillation when the amount of Ang-2 measured in the subject is equal to or greater than the reference amount of Ang-2, and
   d) administering at least one anticoagulant to the subject identified to be at risk.

2. The method of claim 1, wherein the amounts of BNP or NT-proBNP and Angiopoietin-2 are measured.

3. The method of claim 1, wherein the amounts of Angiopoietin-2 and Angiopoietin-1 are measured, and optionally wherein a ratio of the amount of Angiopoietin-2 and the amount of Angiopoietin-1 is calculated and wherein said calculated ratio is compared to a reference ratio.

4. A method for administering and monitoring a therapy that aims to reduce the risk of recurrence of Atrial Fibrillation in a subject receiving the therapy, said method comprising
   (a) administering a therapy that aims to reduce the risk of recurrence of Atrial Fibrillation in the subject,
   (b) measuring an amount of Angiopoietin-2 (Ang-2) and optionally measuring an amount of at least one further biomarker selected from the group consisting of Angiopoietin-1 (Ang-1), BNP, NT-proBNP, CK-MB (Muscle-Brain type Creatine Kinase), IGFBP-7(Insulin-like Growth Factor Binding Protein 7) and cardiac Troponin in a first serum or plasma sample from the subject who has a known history of atrial fibrillation, and who has normal sinus rhythm when the sample is obtained,
   (c) measuring the amount(s) of the biomarker(s) as determined in step (a) in a second serum or plasma sample from the subject,
   (d) comparing the amount(s) of the biomarker(s) as measured in the first sample to the amount(s) of said biomarker(s) in said second sample, and
   (e) monitoring the therapy based on the results of step c) wherein the amount of the Ang-2 in the second sample equal to or greater than the amount of the Ang-2 in the first sample indicates that the subject is not responding to the therapy and wherein the amount of the Ang-2 in the second sample below the amount of the Ang-2 in the first sample indicates that the subject is responding to the therapy.

5. The method of claim 4, wherein the therapy is at least one anticoagulant.

6. The method of claim 4, wherein the at least one further biomarker is selected from the group consisting of BNP, NT-proBNP, CK-MB (Muscle-Brain type Creatine Kinase), IGFBP-7 (Insulin-like Growth Factor Binding Protein 7) and a cardiac Troponin.

7. The method of claim 4, wherein the at least one further biomarker is Ang-1.

8. The method of claim 1, wherein the at least one anticoagulant is selected from the group consisting of heparin, a coumarin derivative, a tissue factor pathway inhibitor (TFPI), antithrombin III, factor IXa inhibitors, factor Xa inhibitors, inhibitors of factors Va and VIIIa and thrombin inhibitors.

9. The method of claim 5, wherein the at least one anticoagulant is selected from the group consisting of heparin, a coumarin derivative, a tissue factor pathway inhibitor (TFPI), antithrombin III, factor IXa inhibitors, factor Xa inhibitors, inhibitors of factors Va and VIIIa and thrombin inhibitors.

* * * * *